United States Patent
Moon et al.

(10) Patent No.: US 10,072,118 B2
(45) Date of Patent: Sep. 11, 2018

(54) POLYCYCLOHEXYLENEDIMETHYLENE TEREPHTHALATE RESIN HAVING ENHANCED CRYSTALLIZATION SPEED AND METHOD FOR PREPARING SAME

(71) Applicant: SK CHEMICALS CO., LTD., Gyeonggi-do (KR)

(72) Inventors: Jung-Me Moon, Gyeonggi-do (KR); Tae-Young Kim, Gyeonggi-do (KR); Su-Min Lee, Gyeonggi-do (KR)

(73) Assignee: SK Chemicals Co., Ltd. (KR)

( * ) Notice: Subject to any disclaimer, the term of this patent is extended or adjusted under 35 U.S.C. 154(b) by 0 days.

(21) Appl. No.: 15/520,181

(22) PCT Filed: Oct. 23, 2015

(86) PCT No.: PCT/KR2015/011270
§ 371 (c)(1),
(2) Date: Apr. 19, 2017

(87) PCT Pub. No.: WO2016/064241
PCT Pub. Date: Apr. 28, 2016

(65) Prior Publication Data
US 2017/0306083 A1    Oct. 26, 2017

(30) Foreign Application Priority Data

Oct. 23, 2014  (KR) ........................ 10-2014-0144231

(51) Int. Cl.
| | | |
|---|---|---|
| *C08G 63/85* | (2006.01) | |
| *C08G 63/127* | (2006.01) | |
| *C08G 63/86* | (2006.01) | |
| *G01N 25/48* | (2006.01) | |
| *B01J 23/18* | (2006.01) | |
| *B01J 21/06* | (2006.01) | |

(52) U.S. Cl.
CPC ........... *C08G 63/127* (2013.01); *C08G 63/85* (2013.01); *C08G 63/866* (2013.01); *B01J 21/063* (2013.01); *B01J 23/18* (2013.01); *G01N 25/4866* (2013.01)

(58) Field of Classification Search
USPC .................. 528/271, 272, 279, 285
See application file for complete search history.

(56) References Cited

U.S. PATENT DOCUMENTS

| 4,143,093 A | 3/1979 | Ruter |
|---|---|---|
| 4,223,113 A | 9/1980 | Bier et al. |
| 4,223,125 A | 9/1980 | Bier et al. |
| 4,806,589 A | 2/1989 | Chen |
| 5,242,967 A | 9/1993 | Minnick |
| 2016/0272787 A1* | 9/2016 | Park .................. C08K 3/22 |

FOREIGN PATENT DOCUMENTS

| EP | 0483354 | | 5/1992 |
|---|---|---|---|
| JP | H0665482 | A | 3/1994 |
| JP | H07-102047 | A | 4/1995 |
| JP | 3360237 | B2 | 12/2002 |
| JP | 5179731 | B2 | 4/2013 |
| JP | 5272425 | B2 | 8/2013 |
| KR | 10-1994-0009232 | A | 5/1994 |
| KR | 10-2011-0119627 | A | 11/2011 |
| KR | 10-2012-0033628 | | 4/2012 |
| KR | 10-2012-0088734 | A | 8/2012 |
| KR | 10-2014-0070455 | A | 6/2014 |
| KR | 10-2015-0054697 | A | 5/2015 |

OTHER PUBLICATIONS

International Search Report prepared by the Korean Intellectual Property Office dated Dec. 23, 2015, for International Application No. PCT/KR2015/011270.
Extended Search Report for European Patent Application No. 15852437.1, dated Apr. 17, 2018, 6 pages.

* cited by examiner

*Primary Examiner* — Terressa M Boykin
(74) *Attorney, Agent, or Firm* — Sheridan Ross P.C.

(57) ABSTRACT

The present invention relates to a polycyclohexylenedimethylene terephthalate (PCT) resin having enhanced crystallization speed and a method for preparing same. A PCT resin, according to an embodiment of the present invention, comprises: a reactant of (A) a dicarboxylic acid compound or a dicarboxylic acid ester compound and (B) a diol compound total of which 90 mol % or more is cyclohexanedimethanol; and 10-1000 ppm of antimony (Sb) atoms on the basis of the total weight of the resin, wherein the differential between the melting point (Tm) and a reduced crystallization temperature (Tmc) is 45° C. or lower. A PCT resin, according to the present invention, has high crystallization speed and thus enables fast production of various molded products. In particular, the PCT resin has high crystallization temperature and high heat resistance and thus enables fast production of a high-quality heat-resistant molded product by means of injection molding.

13 Claims, No Drawings

POLYCYCLOHEXYLENEDIMETHYLENE TEREPHTHALATE RESIN HAVING ENHANCED CRYSTALLIZATION SPEED AND METHOD FOR PREPARING SAME

CROSS REFERENCE TO RELATED APPLICATIONS

This application is a national stage application under 35 U.S.C. 371 and claims the benefit of PCT Application No. PCT/KR2015/011270 having an international filing date of 23 Oct. 2015, which designated the United States, which PCT application claimed the benefit of Korean Patent Application No. 10-2014-0144231 filed 23 Oct. 2014, the disclosures of each of which are incorporated herein by reference.

TECHNICAL FIELD

The present invention relates to a polycyclohexylenedimethylene terephthalate resin having an enhanced crystallization speed and a method for preparing the same.

BACKGROUND ART

Poly(alkylene terephthalate) is used as a material for fibers, films, and molded articles, etc., due to excellent physical properties such as abrasion resistance, durability, and thermal stability, etc. Examples of the poly(alkylene terephthalate) include poly(ethylene terephthalate) (hereinafter, referred to as PET), poly(butylene terephthalate) (hereinafter, referred to as PBT), poly(1,4-cyclohexylenedimethylene terephthalate) (hereinafter, referred to as PCT), etc., that are commercially available. The most widely used material among them is PET, which is used for fiber, and bottle, etc.

The PET has a slow crystallization speed despite excellent physical properties thereof, and thus, when the PET is attempted to be used for engineering plastics requiring high crystallinity, a nucleating agent, a crystallization accelerator, etc., should be essentially used, and a mold temperature should be controlled due to a reduced production speed during an injection molding process.

On the other hand, the PBT has been widely used for the above-described engineering plastics since the crystallization speed of the PCT is faster than that of the PET. However, the PBT has a lower heat deflection temperature compared to the PET, and thus, the use thereof is limited for applications requiring a high degree of heat resistance despite excellent moldability as compared to the PET.

Accordingly, a method of improving moldability by adding various nucleating agents to a PCT resin having a high heat deflection temperature has been proposed to compensate for poor moldability and low heat deflection temperature of the PET and the PBT. Specifically, Patent Document 1 discloses a method of using an aliphatic polyester having a number average molecular weight of 8,000 or more as a nucleating agent to improve the crystallization speed of the PCT. Patent Document 2 discloses a poly(alkylene terephthalate) composition using an aromatic polyester as a nucleating agent. In addition, Patent Document 3 discloses a poly(alkylene terephthalate) composition including an oligomer polyester having a number average molecular weight of 4,000 or less.

However, Patent Documents 1 to 3 propose a composition for improving a crystallization speed of PCT by adding various nucleating agents to the PCT in a compounding step, and thus, the crystallization speed of the PCT itself is not improved. Therefore, it is necessary to provide a fundamental solution for improving the crystallization speed of the PCT itself.

RELATED ART DOCUMENT

Patent Document

U.S. Pat. No. 5,242,967
U.S. Pat. No. 4,223,125
U.S. Pat. No. 4,223,113

DISCLOSURE

Technical Problem

The present invention has been made in an effort to provide a polycyclohexylenedimethylene terephthalate (PCT) resin and a method for preparing the same having advantages of having an enhanced crystallization speed.

Technical Solution

An exemplary embodiment of the present invention provides a polycyclohexylenedimethylene terephthalate resin including: a reaction product of (A) a dicarboxylic acid compound or a dicarboxylic acid ester compound and (B) a diol compound in which at least 90 mol % of the total diol compound is cyclohexanedimethanol; and 10 to 1000 ppm of antimony (Sb) atoms relative to a weight of the resin, wherein a difference between a melting point (Tm) and a melt crystallization temperature (Tmc) is 45° C. or less.

An intrinsic viscosity value at 35° C. measured after dissolving the polycyclohexylenedimethylene terephthalate (PCT) resin in an o-chlorophenol solution at a concentration of 1.2 g/dl may be 0.35 dl/g or more.

A half-crystallization time ($t_{1/2}$) may be 10 to 90 seconds, the half-crystallization time obtained by drawing an Avrami plot using a crystallization peak according to time which is obtained by increasing a temperature of the resin up to 320° C. at 10° C./min, maintaining the temperature at 320° C. for 2 minutes, decreasing the temperature up to 220° C. to 240° C. at −200° C./min to perform crystallization at 220° C. to 240° C. for 30 minutes, and then, decreasing the temperature up to 40° C. at −200° C./min, maintaining the temperature for 5 minutes, and increasing the temperature up to 320° C. at 10° C./min, using a differential scanning calorimeter (DSC), and then, calculating a crystallization speed constant (k) and an Avrami exponent (n) from an Avrami Equation represented by Equation 1 below, and substituting the crystallization speed constant (k) and the Avrami exponent (n) in Equation 2:

$$x(t) = 1 - e^{-k(t)^n} \quad \text{[Equation 1]}$$

$$t_{1/2} = (\ln 2/k)^{(1/n)} \quad \text{[Equation 2]}$$

Another exemplary embodiment of the present invention provides a method for preparing a polycyclohexylenedimethylene terephthalate resin including: a reaction step of reacting a mixture including (A) a dicarboxylic acid compound or a dicarboxylic acid ester compound, (B) a diol compound in which at least 90 mol % of the total diol compound is cyclohexanedimethanol, (C) a phosphorus stabilizer, and (D) an antimony-based catalyst added at 10 to 1000 ppm relative to a weight of the resin based on an antimony (Sb) atom; and a polycondensation step of polycondensing a reaction product obtained by the reaction.

A unit of ppm relative to the weight of the resin in the present specification means a weight corresponding to one millionth of the total weight of the PCT resin. For example, a specific substance is included in a content of 1 ppm in 1000 g of the PCT resin, which means that a weight of the specific substance is 1 mg. In addition, when it is described that a content of a substance such as a catalyst or a stabilizer used in a process for preparing a PCT resin is expressed in ppm relative to the weight of the resin, the ppm may be understood as ppm based on a theoretical weight of the PCT resin calculated from contents of a monomer, etc., used in the process for preparing the corresponding PCT resin.

The phosphorus stabilizer may be at least one selected from the group consisting of a phosphoric acid, a phosphorous acid, triethyl phosphate, trimethyl phosphate, triphenyl phosphate, and triethyl phosphonoacetate.

The phosphorus stabilizer may be added at 0.1 to 30 ppm relative to the weight of the resin based on a phosphorus (P) atom.

The antimony-based catalyst may be at least one selected from the group consisting of antimony trioxide, antimony tetraoxide, and antimony pentaoxide.

In the reaction step of reacting the mixture, a titanium-based catalyst may be further added.

The titanium-based catalyst may be at least one selected from the group consisting of titanium oxide, tetra-n-propyl titanate, tetra-isopropyl titanate, tetra-n-butyl titanate, tetra-isobutyl titanate, and butyl-isopropyl titanate. The titanium-based catalyst may be added at 0.1 to 40 ppm relative to the weight of the resin based on a titanium (Ti) atom.

The polycondensation step of polycondensing a reaction product may be performed at a temperature of 290 to 320° C. and under a pressure of 0.1 to 2.0 torr for 100 to 300 minutes.

Yet another exemplary embodiment of the present invention provides a polycyclohexylenedimethylene terephthalate compound resin including: the polycyclohexylenedimethylene terephthalate resin as described above; and at least one selected from the group consisting of an organic filler and an inorganic filler.

Yet another exemplary embodiment of the present invention provides a molded article manufactured by using the polycyclohexylenedimethylene terephthalate compound resin as described above.

Advantageous Effects

The polycyclohexylenedimethylene terephthalate resin according to the present invention may have a high crystallization speed, thereby manufacturing various molded articles at a high production speed. In particular, the PCT resin of the present invention may have a high crystallization temperature and high heat resistance, thereby manufacturing a high-quality heat-resistant molded article at a high speed using an injection molding method.

MODE FOR INVENTION

Although the present invention may be modified variously and have several embodiments, the exemplary embodiments are illustrated in the accompanying drawings and will be described in detail in the detailed description. However, the present invention is not limited to the specific embodiments and should be construed as including all the changes, equivalents, and substitutions included in the spirit and scope of the present invention. Further, when it is determined that the detailed description of the known art related to the present invention may obscure the gist of the present invention, the detailed description thereof will be omitted.

A polycyclohexylenedimethylene terephthalate resin according to an exemplary embodiment of the present invention includes a reaction product of (A) a dicarboxylic acid compound or a dicarboxylic acid ester compound and (B) a diol compound in which at least 90 mol % of the total diol compound is cyclohexanedimethanol; and 10 to 1000 ppm of antimony (Sb) atoms relative to a weight of the resin, wherein a difference between a melting point (Tm) and a melt crystallization temperature (Tmc) is 45° C. or less.

In addition, a method for preparing a polycyclohexylenedimethylene terephthalate resin according to another exemplary embodiment of the present invention includes: a reaction step of reacting a mixture including (A) a dicarboxylic acid compound or a dicarboxylic acid ester compound, (B) a diol compound in which at least 90 mol % of the total diol compound is cyclohexanedimethanol, (C) a phosphorus stabilizer, and (D) an antimony-based catalyst added at 10 to 1000 ppm relative to a weight of the resin based on an antimony (Sb) atom; and a polycondensation step of polycondensing a reaction product obtained by the reaction.

Hereinafter, the polycyclohexylenedimethylene terephthalate resin (PCT resin) and the method for preparing the same according to a specific exemplary embodiment of the present invention will be described in more detail.

The PCT resin has excellent heat resistance, chemical resistance, hygroscopicity resistance, and flowability, as compared to general-purpose polyesters such as PET and PBT. In particular, the PCT resin has a very high heat deflection temperature of 245 to 260° C., and a continuous-use temperature of 130 to 150° C., and is classified as an only metal-replaceable engineering plastic among non-wholly aromatic polyesters that are commercially available, except for liquid crystalline polyesters. The PCT resin has excellent color stability and has a low water absorption rate (relative to polyamide) as compared to other resins, which may be effectively utilized for electronic materials that require a surface mounting technology that is performed at a high-temperature or for housing or for a reflector of a light emitting diode (LED) that is continuously exposed to heat and light during driving.

However, conventional PCT resin has a problem in that a crystallization speed is not sufficiently high. Therefore, various methods for adding additives to improve the crystallization speed of the PCT resin in a compounding step have been proposed in the technical field of the present invention. However, a fundamental solution for improving a crystallization temperature of the PCT resin itself has not been developed.

Accordingly, the present inventors confirmed through experiments that when a PCT resin was prepared using a specific combination of monomers and catalyst of the PCT resin, the crystallization speed of the PCT resin itself could be improved, and completed the present invention.

The polycyclohexylenedimethylene terephthalate resin according to an exemplary embodiment of the present invention includes a reaction product of (A) a dicarboxylic acid compound or a dicarboxylic acid ester compound and (B) a diol compound in which at least 90 mol % of the total diol compound is cyclohexanedimethanol; and 10 to 1000 ppm of antimony (Sb) atoms relative to a weight of the resin, wherein a difference between a melting point (Tm) and a melt crystallization temperature (Tmc) is 45° C. or less.

The PCT resin may be prepared by an esterification reaction of the dicarboxylic acid compound and the diol compound or by a transesterification reaction of the dicarboxylic acid ester compound and the diol compound as described below. In particular, in the PCT resin, at least 90 mol % of the total diol compound participating in the polymerization of the PCT resin may be cyclohexanedimethanol. Further, the PCT resin may include 10 to 1000 ppm of antimony (Sb) atoms relative to the weight of the resin. When the total diol compound participating in the polymerization of the PCT resin includes the cyclohexanedimethanol in a content of less than 90 mol %, or when the PCT resin includes the antimony atoms in a content of less than 10 ppm relative to the weight of the resin, an effect of improving the crystallization speed of the PCT resin may not be significant. Further, when the PCT resin includes the antimony atoms in a content of more than 1000 ppm relative to the weight of the resin, a color of the PCT resin becomes very dark. More preferably, the content of antimony atoms included in the PCT resin may be adjusted to about 70 to 150 ppm relative to the weight of the resin. Within this range, the PCT resin may have a very fast crystallization speed and exhibit bright color. For example, the PCT resin including the antimony atoms in the above-described range may have a Color-L* value of 70 or more as measured after heat treatment at 150° C. for 1 hour.

The PCT resin including the specific combination of reaction product of monomers and the antimony may have a high melt crystallization temperature (Tmc) close to the melting point (Tm). Specifically, the PCT resin may have a difference between the melting point (Tm) and the melt crystallization temperature (Tmc) of 45° C. or less. The PCT resin may have a fast crystallization speed due to the high crystallization temperature. As an example, the PCT resin may have a half-crystallization time of 10 to 90 seconds, 10 to 85 seconds, or 10 to 70 seconds. As described above, the PCT resin having a short half-crystallization time may be crystallized at a high speed in a molding step, and a production speed of the product may be remarkably improved.

The half-crystallization time may be obtained through the following procedures. First, a temperature of the resin is increased up to a temperature equal to or higher than the melting point (Tm) of the resin at a predetermined speed by using a differential scanning calorimeter (DSC). Then, the temperature of the resin is decreased to a temperature equal to or lower than the melt crystallization temperature (Tmc) of the resin, and the resin of which the temperature is decreased is crystallized at a predetermined temperature equal to or lower than the Tmc of the resin. Then, the temperature of the crystallized resin is decreased again up to about 40° C. at a predetermined speed and maintained for a predetermined time, and then, the temperature of the resin is increased up to a temperature equal to or higher than the melting point of the resin at a predetermined speed. Next, an Avrami plot is drawn using a crystallization peak according to time obtained in this process. The Avrami plot may be used to calculate a crystallization speed constant (k) and an Avrami exponent (n) in an Avrami Equation represented by Equation 1 below, and the crystallization speed constant (k) and the Avrami exponent (n) may be substituted in Equation 2, thereby calculating the half-crystallization time ($t_{1/2}$):

$$x(t)=1-e^{-k(t)^n}$$ [Equation 1]

$$t_{1/2}=(\ln 2/k)^{(1/n)}$$ [Equation 2]

The PCT resin according to an exemplary embodiment of the present invention may have a high melt crystallization temperature of, for example, about 220° C. or higher or about 240° C. or higher. Accordingly, the half-crystallization time of the PCT resin according to an exemplary embodiment may be obtained by using the crystallization peak according to time which is obtained by increasing a temperature of the resin up to 320° C. at 10° C./min, maintaining the temperature at 320° C. for 2 minutes, decreasing the temperature up to 220° C. to 240° C. at −200° C./min to perform crystallization at 220° C. to 240° C. for 30 minutes, and then, decreasing the temperature up to 40° C. at −200° C./min, maintaining the temperature for 5 minutes, and increasing the temperature up to 320° C. at 10° C./min, using a differential scanning calorimeter (DSC).

In addition, in the PCT resin, an intrinsic viscosity value at 35° C. measured after dissolving the resin in an o-chlorophenol solution at a concentration of 1.2 g/dl may be 0.35 dl/g or more. An upper limit of the intrinsic viscosity value is not particularly limited, and may be controlled to 2.0 dl/g or less for proper flowability and handling.

A method for preparing a polycyclohexylenedimethylene terephthalate resin according to another exemplary embodiment of the present invention includes: a reaction step of reacting a mixture including (A) a dicarboxylic acid compound or a dicarboxylic acid ester compound, (B) a diol compound in which at least 90 mol % of the total diol compound is cyclohexanedimethanol, (C) a phosphorus stabilizer, and (D) an antimony-based catalyst added at 10 to 1000 ppm relative to a weight of the resin based on an antimony (Sb) atom; and a polycondensation step of polycondensing a reaction product obtained by the reaction.

The non-wholly aromatic polyester resin may be generally polymerized from the dicarboxylic acid (A) and the diol compound (B) as known in the art. The dicarboxylic acid (A) may be mainly terephthalic acid (TPA). However, the dicarboxylic acid (A) may include a small content of isophthalic acid (IPA), 2,6-naphthalenedicarboxylic acid (2,6-NDA), or a mixture thereof. Specifically, at least 90 mol % of the total dicarboxylic acid may be terephthalic acid. In addition, the dicarboxylic acid (A) may include other dicarboxylic acids in a content of 10 mol % or less in the total dicarboxylic acid, in addition to the terephthalic acid.

In the present specification, the content of the monomers may be a content of monomers injected into a reactor, or a content of the monomers remaining in the reactor after some of the monomers injected into the reactor are discharged by evaporation, etc. Among them, for easy preparation of the PCT resin having desired physical properties, the content of the monomers may mean the content of the monomers remaining in the reactor. Further, the content of the monomers remaining in the reactor may be confirmed from a molar ratio or a weight ratio of repeating units included in a finally prepared PCT resin.

The diol compound (B) may be mainly cyclohexanedimethanol. However, the diol compound (B) may include a small content of other diol compounds such as at least one selected from the group consisting of ethylene glycol, diethylene glycol, 1,4-butanediol, 1,3-propanediol, and neopentyl glycol. Specifically, at least 90 mol % of the total diol compound may be cyclohexanedimethanol. In addition, the diol compound (B) may include other diol compounds in a content of 10 mol % or less in the total diol compound, in addition to the cyclohexanedimethanol. In particular, a PCT resin having a higher crystallization temperature may be provided by using at least 90 mol % of the total diol compound as cyclohexanedimethanol.

In addition to the esterification reaction of the dicarboxylic acid and the diol compound, the PCT resin may also be synthesized by a transesterification reaction of the dicarboxylic acid ester compound (A) and the diol compound (B). As the dicarboxylic acid ester compound (A), dimethyl terephthalate (DMT) may be mainly used. However, similar to the case of the dicarboxylic acid, the dicarboxylic acid ester compound (A) may also include a small content of dimethyl isophthalate (DMI), dimethyl 2,6-naphthalenedicarboxylate (2,6-NDC), or a mixture thereof. Specifically, at least 90 mol % of the total dicarboxylic acid ester compound may be dimethyl terephthalate. In addition, the dicarboxylic acid ester compound (A) may include other dicarboxylic acid ester compounds in a content of 10 mol % or less in the total dicarboxylic acid ester compounds.

As the phosphorus stabilizer (C), a phosphoric acid such as a phosphoric acid, a phosphorous acid, or the like, a phosphoric acid ester-based compound such as triethyl phosphate, trimethyl phosphate, triphenyl phosphate, or triethyl phosphonoacetate, or the like, may be used. The phosphorus stabilizer (C) may be added at 0.1 to 30 ppm relative to the weight of the resin based on a phosphorus (P) atom.

The phosphorus stabilizer (C) is used in the content within the above-described range, which does not affect an activity of the catalyst, and thus, side reactions that may affect a quality of the resin may be prevented without deteriorating a reaction speed and a degree of polymerization.

On the other hand, the phosphorus stabilizer (C) may be added at the beginning of or before the esterification reaction or the transesterification reaction. As a result, it is possible to effectively suppress the side reactions that may occur during the esterification reaction or the transesterification reaction at a high temperature.

Examples of the antimony-based catalyst (D) may include at least one selected from the group consisting of antimony trioxide, antimony tetraoxide, and antimony pentaoxide.

This antimony-based catalyst is added so that the antimony (Sb) atoms are included at a content of 10 to 1000 ppm in a finally prepared resin. If the content of the antimony-based catalyst is less than the above-described range, a melt crystallization speed of the PCT resin may not be improved. If the content of the antimony-based catalyst is more than the above-described range, a color of the finally prepared resin may become dark.

A titanium-based catalyst may be further added to the mixture including the dicarboxylic acid compound or dicarboxylic acid ester compound (A), the diol compound (B), the phosphorus stabilizer (C), and the antimony-based catalyst (D).

The titanium-based catalyst may be at least one selected from the group consisting of titanium oxide, tetra-n-propyl titanate, tetra-isopropyl titanate, tetra-n-butyl titanate, tetra-isobutyl titanate, and butyl-isopropyl titanate. The titanium-based catalyst may be added at 0.1 to 40 ppm relative to the weight of the resin based on a titanium (Ti) atom in order to control a side reaction that causes discoloration. If the content of the titanium-based catalyst is less than the above-described range, a reaction speed is reduced. If the content of the titanium-based catalyst is more than the above-described range, a color of the resin may be deteriorated and a pyrolysis reaction may occur.

In addition to the above-described components, the mixture may further include other additives generally used in the art to which the present invention pertains.

In the reaction step of reacting the mixture, the mixture may be reacted by using a method widely known in the art to which the present invention pertains. As an example, the reaction step of reacting the mixture may include adding the above-described components to a prepared tank and stirring to prepare the mixture. Here, the phosphorus stabilizer may be injected into the tank in advance, and the dicarboxylic acid compound or the dicarboxylic acid ester compound (A) and the diol compound (B) may be stably mixed.

The reaction step of reacting the mixture may include an esterification reaction or a transesterification reaction using the mixture prepared as described above under facilities and reaction conditions known in the art to which the present invention pertains. Specifically, the mixture may be heated to a temperature of from 230 to 290° C. under a pressure of from 0 to 0.3 MPa (0 to 2,206.7 torr) to perform the esterification reaction or the transesterification reaction between the compound (A) and the compound (B). When the reaction step of reacting the mixture proceeds in such a manner that the mixture is subjected to the esterification reaction, a system may be configured so that water generated during the esterification reaction is immediately removed.

In the reaction step of reacting the mixture, the mixture may be heated to the above-described temperature in the above-described pressure range until the esterification reaction or the transesterification reaction proceeds to about 90% or more. As an example, the mixture may be heated to the above-described temperature in the above-described pressure range for about 1 to 10 hours.

When a desired reaction proceeds at least about 90% in the reaction step of reacting the mixture, a polycondensation step of polycondensing a reaction product obtained by the reaction may be performed. The polycondensation step of polycondensing the reaction product may include transferring the reaction product to a polycondensation reactor. The reaction product transferred to the polycondensation reactor may be heated to a temperature of 290 to 320° C. under a pressure of about 0.1 to 2.0 torr. The reaction product transferred to the polycondensation reactor may be polycondensed until the degree of polymerization reaches about 100 or more. Specifically, the reaction product may be polycondensed by heating at the above-described temperature in the above-described pressure range for about 100 to 300 minutes.

The method for preparing the PCT resin may further include a step of preparing a pellet by extruding the polycondensation reaction product, after the polycondensation step of polycondensing the reaction product. As an example, the pellet prepared in the above-described step may have an intrinsic viscosity at 35° C. of 0.35 to 2.0 dl/g as measured after dissolving the pellet in an o-chlorophenol solution at a concentration of 1.2 g/dl.

In addition, the method for preparing the PCT resin may further include a step of performing solid-phase polymerization by crystallizing the pellet after the step of preparing the pellet, if necessary.

The solid-phase polymerization may include heating the crystallized pellet to a temperature of 230 to 270° C. under a pressure of 0.2 to 2.0 torr in a nitrogen atmosphere. The PCT resin prepared through the solid-phase polymerization step may have an intrinsic viscosity value at 35° C. of 0.7 to 2.0 dl/g as measured after dissolving the pellet in the o-chlorophenol solution at a concentration of 1.2 g/dl.

The method for preparing the PCT resin may further include a step that is conventionally employed in the art to which the present invention pertains, in addition to the above-described steps.

The PCT resin may be mixed with conventional organic fillers and/or inorganic fillers to provide a PCT compound resin. Examples of the organic fillers and the inorganic fillers may include a glass fiber, titanium oxide, a compatibilizer, a stabilizer, a mixture thereof, etc. However, since the PCT compound resin includes the PCT resin having a rapid crystallization speed, a conventional nucleating agent used for improving the crystallization speed of the PCT resin may not be included, or may be included in a smaller content as compared to the related art. Therefore, by using the PCT compound resin, it is possible to provide various molded articles at a high preparation speed.

Hereinafter, preferable exemplary embodiments of the present invention will be described in detail. However, these Examples are only to illustrate the present invention and the scope of the present invention is not construed to be limited to these examples.

EXAMPLE 1

2.0 kg of 1,4-cyclohexanedimethanol (trans 70%), 1.8 kg of terephthalic acid, 0.4 g of triethylphosphate, 0.2 g of a titanium oxide-based catalyst (Hombifast PC from Sachtleben, 15 wt % of Ti atomic content in the catalyst) 0.2 g of antimony trioxide (83.5 wt % of antimony atomic content in the catalyst) were injected into a reactor, and an esterification reaction was performed by increasing a temperature up to 280° C. at normal pressure for 3 hours. Then, the esterification reaction product was polycondensed by heating the esterification reaction product at a temperature of 295° C. under a pressure of 0.5 to 1 torr for 150 minutes to prepare a PCT resin.

EXAMPLE 2

A PCT resin was prepared in the same manner as in Example 1, except that the content of the titanium oxide-based catalyst in Example 1 was changed to 0.1 g.

EXAMPLE 3

A PCT resin was prepared in the same manner as in Example 2, except that the content of the antimony trioxide in Example 2 was changed to 0.4 g.

EXAMPLE 4

A PCT resin was prepared in the same manner as in Example 1, except that the content of the antimony trioxide in Example 1 was changed to 0.4 g.

EXAMPLE 5

A PCT resin was prepared in the same manner as in Example 1, except that the content of the antimony trioxide in Example 1 was changed to 1.4 g.

EXAMPLE 6

A PCT resin was prepared in the same manner as in Example 4, except that 400 g of 2.0 kg of 1,4-cyclohexanedimethanol in Example 4 was substituted with 260 g of ethylene glycol.

COMPARATIVE EXAMPLE 1

A PCT resin was prepared in the same manner as in Example 1, except that the antimony trioxide in Example 1 was not used.

COMPARATIVE EXAMPLE 2

A PCT resin was prepared in the same manner as in Example 1, except that 300 g of 2.0 kg of 1,4-cyclohexanedimethanol in Example 1 was substituted with 280 g of ethylene glycol.

COMPARATIVE EXAMPLE 3

A PCT resin was prepared in the same manner as in Example 1, except that the content of the antimony trioxide in Example 1 was changed to 0.02 g.

EXPERIMENTAL EXAMPLE

Physical properties of the PCT resins obtained in Examples and Comparative Examples as described above were measured by the following methods and shown in Table 1 below.

(1) Measurement of intrinsic viscosity: the PCT resin was dissolved in o-chlorophenol at a concentration of 1.2 g/dl, and an intrinsic viscosity thereof was measured at 35° C. using a Ubbelohde viscometer.

(2) Color measurement: the PCT resin was crystallized in a convection oven at 150° C. for 1 hour, and then, the color of the PCT resin was measured using a color meter. Color-L* measured after heat treatment at 150° C. for 1 hour means contrast, indicating that as the value is higher, the color is closer to white. On the other hand, Color-b* measured after heat treatment at 150° C. for 1 hour means that when the value is negative, it is close to blue, and when the value is positive, it is close to yellow.

(3) Measurement of melting point (Tm) and melt crystallization temperature (Tmc): a temperature of an endothermic curve peak obtained by using a differential scanning calorimeter (DSC) when a sample was filled in an aluminum pan, and a temperature of the sample was increased up to 320° C. at 10° C./min and maintained at 320° C. for 2 minutes, and then, the temperature thereof was decreased up to 30° C. at −150° C./min, and increased up to 320° C. at 10° C./min, was determined as the melting point (Tm). Subsequently, a temperature of an exothermic curve peak when the temperature of the sample was maintained at 320° C. for 2 minutes, and then, decreased up to 30° C. at −10° C./min, was determined as the melt crystallization temperature (Tmc).

(4) Measurement of half-crystallization speed: the sample was filled in an aluminum pan, and a temperature of the sample was increased up to 320° C. at 10° C./min and maintained at 320° C. for 2 minutes, and then, the temperature thereof was decreased up to 200 to 240° C. at −200° C./min to perform crystallization at any specific temperature between 200° C. and 240° C. for 30 minutes, and the temperature thereof was decreased up to 40° C. at −200° C./min and maintained for 5 minutes, using a differential scanning calorimeter (DSC). The crystallization temperature was determined in consideration of the melt crystallization temperature of the sample. In Examples 1 to 5, the sample was crystallized at 240° C. In Example 6, the sample was crystallized at 225° C. In Comparative Examples 1 and 3, the sample was crystallized at 230° C., and in Comparative Example 2, the sample was crystallized at 200° C.

Then, the temperature of the crystallized sample was increased up to 320° C. at a speed of 10° C./min to obtain a crystallization peak according to time. The crystallization peak obtained by the method was used to draw an Avrami plot, and then, a crystallization speed constant (k) and an Avrami exponent (n) were calculated from the Avrami equation represented by Equation 1 below, and the crystallization speed constant (k) and the Avrami exponent (n) were substituted in Equation 2 below to obtain a half-crystallization time ($t_{1/2}$) at which a crystallization degree is 0.5:

$$x(t)=1-e^{-k(t)^n} \quad \text{[Equation 1]}$$

$$t_{1/2}=(\ln 2/k)^{(1/n)} \quad \text{[Equation 2]}$$

TABLE 1

| Unit | CHDM content (a) mol % | Ti content [ppm] | Sb content [ppm] | Intrinsic viscosity [dl/g] | Color-L* after heat treatment at 150° C. for 1 hour | Color-b* after heat treatment at 150° C. for 1 hour | Tm [° C.] | Tmc [° C.] | Tm − Tmc [° C.] | Half-crystallization time [sec] |
|---|---|---|---|---|---|---|---|---|---|---|
| Example 1 | 100 | 30 | 50 | 0.78 | 78.6 | −0.8 | 287 | 244 | 43 | 85 |
| Example 2 | 100 | 15 | 50 | 0.62 | 78.5 | −1.9 | 286 | 246 | 40 | 85 |
| Example 3 | 100 | 15 | 100 | 0.73 | 73.0 | −2.9 | 286 | 246 | 40 | 68 |
| Example 4 | 100 | 30 | 100 | 0.78 | 74.0 | −1.4 | 286 | 250 | 36 | 68 |
| Example 5 | 100 | 30 | 400 | 0.77 | 55.6 | −4.9 | 286 | 251 | 35 | 41 |
| Example 6 | 92 | 30 | 100 | 0.75 | 76.5 | −1.2 | 270 | 225 | 45 | 83 |
| Comparative Example 1 | 100 | 30 | 0 | 0.77 | 89.0 | 3.9 | 286 | 231 | 55 | 100 |
| Comparative Example 2 | 85 | 30 | 50 | 0.79 | 88.5 | 5.8 | 265 | 201 | 64 | 340 |
| Comparative Example 3 | 100 | 30 | 5 | 0.78 | 79.0 | 1.2 | 287 | 235 | 52 | 99 |

(a) indicates a content of the residue of cyclohexanedimethanol (CHDM) in the residue of the total diol compound included in the PCT resin, expressed in mol %.

In Example 6, 1600 g (11.1 mol) of CHDM and 260 g (4.2 mol) of ethylene glycol (EG) as the diol compound were injected into the reactor. However, it was confirmed that a part of the EG was removed during the reaction, and the PCT resin prepared in Example 6 included 92 mol % of the residue derived from the CHDM.

In Comparative Example 2, 1,700 g (11.8 mol) of CHDM and 280 g (4.5 mol) of ethylene glycol (EG) as the diol compound were injected into the reactor. However, it was confirmed that a part of the EG was removed during the reaction, and the PCT resin prepared in Comparative Example 2 included 85 mol % of the residue derived from the CHDM.

As shown from results of the Experimental Example, it was confirmed that the PCT resins of Examples prepared by using the mixture in which at least 90 mol % of the total diol compound is cyclohexanedimethanol, and including the antimony atoms had a generally high melt crystallization temperature and a short half-crystallization time of 85 seconds or less. Therefore, it is expected that the PCT resin according to an exemplary embodiment of the present invention may be used to manufacture a large quantity of injection molded articles in a short time due to an improved crystallization speed.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof

What is claimed is:

1. A polycyclohexylenedimethylene terephthalate resin comprising:
   a reaction product of (A) a dicarboxylic acid compound or a dicarboxylic acid ester compound and (B) a diol compound in which at least 90 mol % of the total diol compound is cyclohexanedimethanol; and
   10 to 1000 ppm of antimony atoms relative to a weight of the resin,
   wherein a difference between a melting point and a melt crystallization temperature is 45° C. or less.

2. The polycyclohexylenedimethylene terephthalate resin of claim 1, wherein:
   an intrinsic viscosity value at 35° C. measured after dissolving the resin in an o-chlorophenol solution at a concentration of 1.2 g/dl is 0.35 dl/g or more.

3. The polycyclohexylenedimethylene terephthalate resin of claim 1, wherein:
   a half-crystallization time (t½) is 10 to 90 seconds, the half-crystallization time obtained by drawing an Avrami plot using a crystallization peak according to time which is obtained by increasing a temperature of the resin up to 320° C. at 10° C/min, maintaining the temperature at 320° C. for 2 minutes, decreasing the temperature up to 220° C. to 240° C. at −200° C/min to perform crystallization at 220° C. to 240° C. for 30 minutes, and then, decreasing the temperature up to 40° C. at −200° C/min, maintaining the temperature for 5 minutes, and increasing the temperature up to 320° C. at 10° C/min, using a differential scanning calorimeter, and then, calculating a crystallization speed constant (k) and an Avrami exponent (n) from an Avrami Equation represented by Equation 1 below, and substituting the crystallization speed constant (k) and the Avrami exponent (n) in Equation 2:

$$x(t) = 1 - e - k(t)^n \quad \text{[Equation 1]}$$

$$t^{1/2} = (\ln 2/k)(1/n). \quad \text{[Equation 2]}$$

4. A method for preparing the polycyclohexylenedimethylene terephthalate resin of claim 1 comprising:
   a reaction step of reacting a mixture including (A) a dicarboxylic acid compound or a dicarboxylic acid ester compound, (B) a diol compound in which at least 90 mol % of the total diol compound is cyclohexanedimethanol, (C) a phosphorus stabilizer, and (D) an antimony-based catalyst added at 10 to 1000 ppm relative to a weight of the resin based on an antimony atom; and
   a polycondensation step of polycondensing a reaction product obtained by the reaction.

5. The method of claim 4, wherein:
the phosphorus stabilizer is at least one selected from the group consisting of a phosphoric acid, a phosphorous acid, triethyl phosphate, trimethyl phosphate, triphenyl phosphate, and triethyl phosphonoacetate.

6. The method of claim 4, wherein:
the phosphorus stabilizer is added at 0.1 to 30 ppm relative to the weight of the resin based on a phosphorus atom.

7. The method of claim 4, wherein:
the antimony-based catalyst is at least one selected from the group consisting of antimony trioxide, antimony tetraoxide, and antimony pentaoxide.

8. The method of claim 4, wherein:
in the reaction step, a titanium-based catalyst is further added.

9. The method of claim 8, wherein:
the titanium-based catalyst is selected from the group consisting of titanium oxide, tetra-n-propyl titanate, tetra-isopropyl titanate, tetra-n-butyl titanate, tetra-isobutyl titanate, and butyl-isopropyl titanate.

10. The method of claim 8, wherein:
the titanium-based catalyst is added at 0.1 to 40 ppm relative to the weight of the resin based on a titanium atom.

11. The method of claim 4, wherein:
the polycondensation step is performed at a temperature of 290 to 320° C. and under a pressure of 0.1 to 2.0 torr for 100 to 300 minutes.

12. A polycyclohexylenedimethylene terephthalate compound resin comprising:
the polycyclohexylenedimethylene terephthalate resin of claim 1; and
at least one component selected from the group consisting of an organic filler and an inorganic filler.

13. A molded article manufactured by using the polycyclohexylenedimethylene terephthalate compound resin of claim 12.

* * * * *